United States Patent
Jung et al.

(10) Patent No.: US 11,857,146 B2
(45) Date of Patent: Jan. 2, 2024

(54) BANANA CLIP FOR REMOVING HEMORRHOIDS, AND SURGICAL TOOL SET INCLUDING SAME

(71) Applicant: ENDOVISION CO., LTD., Daegu (KR)

(72) Inventors: Min Ho Jung, Daegu (KR); Chang Young Chae, Gyeongsangbuk-do (KR)

(73) Assignees: Endovision CO., LTD.; Dong Wan Kang

( * ) Notice: Subject to any disclaimer, the term of this patent is extended or adjusted under 35 U.S.C. 154(b) by 415 days.

(21) Appl. No.: 17/260,512

(22) PCT Filed: Apr. 23, 2019

(86) PCT No.: PCT/KR2019/004841
§ 371 (c)(1),
(2) Date: Jan. 14, 2021

(87) PCT Pub. No.: WO2020/017740
PCT Pub. Date: Jan. 23, 2020

(65) Prior Publication Data
US 2021/0267601 A1 Sep. 2, 2021

(30) Foreign Application Priority Data
Jul. 16, 2018 (KR) .................. 10-2018-0082412

(51) Int. Cl.
*A61B 17/122* (2006.01)
*A61B 17/128* (2006.01)
*A61B 17/00* (2006.01)

(52) U.S. Cl.
CPC .......... *A61B 17/122* (2013.01); *A61B 17/128* (2013.01); *A61B 2017/00818* (2013.01)

(58) Field of Classification Search
CPC ................ A61B 17/122; A61B 17/128; A61B 2017/00818; A61B 2017/1225; A61B 2090/037
See application file for complete search history.

(56) References Cited

U.S. PATENT DOCUMENTS 4,870,965 A * 10/1989 Jahanger .............. A61B 17/128
606/174
5,062,846 A 11/1991 Oh et al.
(Continued)

FOREIGN PATENT DOCUMENTS

KR 10-2005-0103214 A 10/2005
KR 10-2017-0051394 A 5/2017
WO 2018117371 A1 6/2018

OTHER PUBLICATIONS

International Search Report for corresponding International Application No. PCT/KR2019/004841; dated Aug. 1, 2019 (5 pages).

*Primary Examiner* — Shaun L David
*Assistant Examiner* — Rachael L Geiger
(74) *Attorney, Agent, or Firm* — Mendelsohn Dunleavy, P.C.

(57) ABSTRACT

Proposed is a banana clip for removing hemorrhoids, and a surgical tool set including the banana clip. The banana clip includes a clip main-body having a first clip arm and a second clip arm, connected to each other by a flexible bending portion in a manner that maintains a predetermined bend angle with respect with each other, which are closed with an outside force in a state where the hemorrhoids to be removed are interposed therebetween and thus are tied tightly around the hemorrhoids; and a holding guide, guiding relative motions of the first clip arm and the second clip arm when the clip main-body is bent inward.

14 Claims, 8 Drawing Sheets

(56) References Cited

U.S. PATENT DOCUMENTS

2018/0103959 A1 4/2018 Raybin et al.
2018/0271532 A1* 9/2018 Shellenberger .... A61B 17/1227

* cited by examiner

BANANA CLIP FOR REMOVING HEMORRHOIDS, AND SURGICAL TOOL SET INCLUDING SAME

TECHNICAL FIELD

The present disclosure relates to a therapeutic tool for removing hemorrhoids and, more particularly, to a surgical tool set including a banana clip for removing hemorrhoids and a structure capable of operating the banana clip in a very short time. The banana clip is tied tightly around the hemorrhoids distinguished from normal tissue. The banana tip is positioned as close as possible to an internal wall of the anus, taking the form of a banana after tied tightly around the hemorrhoids. Thus, no inconvenience is caused in defecation.

BACKGROUND ART

Hemorrhoids are swollen or inflamed vascular structures in the anal canal, which occur due to various causes, and are a disease that causes bleeding, inflammation, severe pain, or various complications. There are two types of hemorrhoids: internal hemorrhoids and external hemorrhoids. The hemorrhoids are treated with various treatment methods, such as band ligation, infrared coagulation, cooling treatment, drug injection, electrotherapy, and surgical incision.

In band ligation, a rubber band is tied tightly around the hemorrhoids to block blood from flowing through the hemorrhoids, and thus the hemorrhoids are separated off naturally. In infrared coagulation, high-temperature heat is applied to blood vessels, thereby fiberizing tissue. In cooling treatment, the hemorrhoids are rapidly cooled using liquid nitrogen or carbon dioxide, and thus are coagulated and destroyed. In drug injection, a curing agent drug, a caustic drug, or the like is injected. In electrotherapy, electrical stimulation is applied inside the hemorrhoids, and thus blood vessels are coagulated. The most important consideration in the treatment methods is that neither pain nor bleeding should occur and normal tissue should not be damaged.

In band ligation, a rubber ring is positioned to encircle the prolapsed hemorrhoids, and thus the hemorrhoids are separated off. The use of the band ligation makes it simple to perform an operation on the hemorrhoids and seldom causes bleeding. However, band ligation has the disadvantage of having a higher recurrence rate than the surgical incision. One of the reasons for this is that, in most cases, the rubber ring is difficult to position as close as possible to roots of the hemorrhoids (according to a position and a shape of the hemorrhoids). Moreover, even if the rubber ring is positioned close to the roots of the hemorrhoids during the operation on the hemorrhoids, in some cases, the position of the rubber ring changes over time.

DISCLOSURE

Technical Problem

An objective of the present disclosure, which is made to solve the above-described problem, is to provide a banana clip for removing hemorrhoids, which is capable of remaining fixed at a fixation point. With this capability, it is possible that the probability of recurrence is greatly reduced and that a reliable remedial effect is provided.

Another objective of the present disclosure is to provide a surgical tool set capable of stably holding a banana clip and thus positioning a banana clip in the vicinity of roots of hemorrhoids by pressing the banana clip against a target region. With this capability, it is possible that an operation time is further shortened and that a satisfactory remedial effect is provided.

Technical Solution

In order to accomplish the above-described objective, according to an aspect of the present disclosure, there is provided a banana clip for removing hemorrhoids, the banana clip including: a clip main-body including a first clip arm and a second clip arm, connected to each other by a flexible bending portion in a manner that maintains a predetermined bend angle with respect with each other, which are closed with an outside force in a state where the hemorrhoids to be removed are interposed therebetween and thus are tied tightly around the hemorrhoids; and a holding guide, connecting the first clip arm and the second clip arm to each other and holding the hemorrhoids in place between the first clip arm and the second clip arm when the clip main-body is bent inward.

In the banana clip, a hook portion and a ligation-keeping portion, which are to be engaged with each other and thus are to maintain a state where the first clip arm and the second clip arm are brought into contact with each other, may be formed on end portions, respectively, of the first clip arm and the second clip arm.

In the banana clip, the hook portion may be formed on the end portion of the first clip arm, and the ligation-keeping portion may be formed on the end portion of the second clip arm, and a guide groove which, immediately before the first and second clip arms are brought into contact with each other, is to be brought into contact with the hook portion and thus is to guide a motion of the hook portion and thus prevent misalignment between the first and second clip arms, may be formed in the ligation-keeping portion, and a center edge portion, which is to be supported on the guide groove while inserted into the guide groove, may be provided on the hook portion.

In the banana clip, a force application portion, transferring an outside force acting thereon to each of the first and second clip arms, may be provided on an end portion of each of the first and second clip arms.

In the banana clip, a guide hole may be formed in the first clip arm in a manner that is pierced in a rotational direction of the first clip arm, and a front-end portion of the holding guide may pass through the guide hole and then may be removably combined with the second clip arm, and, when the first and second clip arms are closed or opened, the holding guide may be supported on an internal surface of the guide hole.

In the banana clip, slippage prevention portions, preventing each of the first and second clip arms from being slid along the hemorrhoids, may be formed on each of respective opposing surfaces of the first and second clip arms.

In the banana clip, the first and second clip arms may be curved to a constant curvature, and a transformation guidance hole may be formed in the bending portion, the transformation guidance hole facilitating transformation of the bending portion and thus preventing concentration of stress on the bending portion when the first and second clip arms are closed.

In order to accomplish the above-described objective, according to another aspect of the present disclosure, there is provided a surgical tool set including: a banana clip including a clip main-body including first and second clip arms, connected to each other by a flexible bending portion in a manner that maintains a predetermined bend angle with respect with each other, which are closed with an outside force in a state where the hemorrhoids to be removed are interposed therebetween and thus are tied tightly around the hemorrhoids, and a holding guide, connecting the first and second clip arms to each other and holding the hemorrhoids in place between the first and second clip arms when the clip main-body is bent inward; and a clip applier, picking up the banana clip, positioning the first and second clip arms in the vicinity of the hemorrhoids to be removed, closing the first and second clip arms, and thus tying the first and second clip arms tightly around the hemorrhoids.

In the surgical tool set, the clip applier may be configured with a pair of applier halves movably fastened together by a connection pin in such a manner as to cross each other, and each of the applier halves may include: a handle;

an extension portion connected to the handle with the connection pin interposed therebetween; and a clip pressing portion, integrally combined with an end portion of the extension portion, pressing the first and second clip arms in a direction of closing the first and second clip arms.

In the surgical tool set, the clip pressing portions may be bent to a predetermined bend angle with respect to the extension portions, respectively, and accommodation slits may be formed in inside surfaces, respectively, of the clip pressing portions, the first and second clip arms being accommodated into and supported on the inside surfaces, respectively, when the banana clip is bent inward.

In the surgical tool set, first pressing protrusions and second pressing protrusions may be provided on an end portion of the first clip arm and an end portion of the second clip arm, respectively, the first pressing protrusions and the second pressing portions, both of which transfer outside forces acting thereon to the first and second clip arms, respectively, and support grooves may be further formed in each of the clip pressing portions, the first pressing protrusions and the second pressing protrusions being accommodated into and supported on the support grooves in one of the clip pressing portions and the support grooves in the other of the clip pressing portions, respectively.

In the surgical tool set, a hook portion and a ligation-keeping portion, which are to be engaged with each other and thus are to maintain a state where the first and second clip arms are brought into contact with each other, may be formed on end portions, respectively, of the first and second clip arms.

In the surgical tool set, the hook portion may be formed on the end portion of the first clip arm, and the ligation-keeping portion mat be formed on the end portion of the second clip arm, and a guide groove, which, immediately before the first and second clip arms are brought into contact with each other, is to be brought into contact with the hook portion and thus is to guide a motion of the hook portion and thus prevent misalignment between the first and second clip arms, may be formed in the ligation-keeping portion, and a center edge portion, which is to be supported on the guide groove while inserted into the guide groove, may be positioned on the hook portion.

In the surgical tool set, a guide hole may be formed in the first clip arm in a manner that is pierced in a rotational direction of the first clip arm, and a front-end portion of the holding guide may pass through the guide hole and then may be removably combined with the second clip arm, and, when the first and second clip arms are closed or opened, the holding guide may be supported on an internal surface of the guide hole.

In the surgical tool set, slippage prevention portions, preventing each of the first and second clip arms from being slid along the hemorrhoids, may be formed on each of respective opposing surfaces of the first and second clip arms.

In the surgical tool set, the first and second clip arms may be curved to a constant curvature, and a transformation guidance hole may be formed in the bending portion, the transformation guidance hole facilitating transformation of the bending portion and thus preventing concentration of stress on the bending portion when the first and second clip arms are closed.

Advantageous Effects

The banana clip for removing hemorrhoids according to the present disclosure, which is configured as described above, has a structure in which the hemorrhoids are positioned between the clip arms that are opened, and then the clip arms are closed. Therefore, the clip arms can be arranged as close as possible to roots of the hemorrhoids. The reliable remedial effect can be provided in that a region subject to removal is completely removed, thereby greatly reducing the probability of recurrence and in that the clip arms are not slid off a once-fixed point. Moreover, the banana clip is positioned close to an internal wall of the anus in a state of being bent like a banana after tied tightly around the hemorrhoids. Thus, no inconvenience is caused in defecation.

The surgical tool set according to the present disclosure is capable of stably holding the banana clip and positioning the banana clip in the vicinity of the roots of the hemorrhoids by pressing the banana clip against a target region. Thus, an operation time can be further shortened.

MODE FOR INVENTION

An embodiment of the present disclosure will be described in more detail below with reference to the accompanying drawings.

Figure 1:
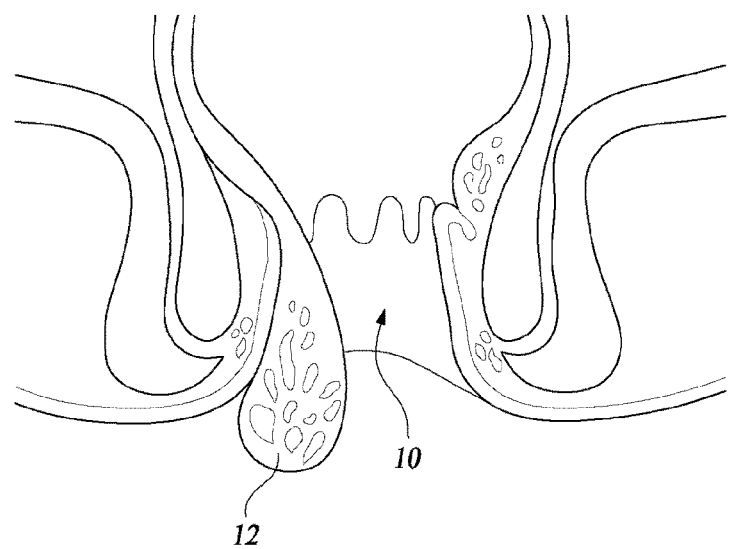
FIG. 1 is a view schematically illustrating the anus where hemorrhoids occur.

FIG. 1 is a reference view schematically illustrating a region of anus 10, where hemorrhoids 12 occur. The hemorrhoids 12, illustrated in FIG. 1, are external hemorrhoids. An application example of a banana clip according to the present embodiment will be described below for convenience in description. However, it is also possible that the banana clip finds application in internal hemorrhoids.

As illustrated, the hemorrhoids 12 are positioned inside the anus 10. As described above, the hemorrhoids 12 are swollen or inflamed vascular structures in the anus 10, which become prolapsed and are exposed to the outside. As illustrated in FIG. 1, the hemorrhoids protrude outward from the anus 10.

A banana clip 50 according to the present embodiment, which will be described below, is tied tightly around roots of the hemorrhoids 12. Accordingly, the banana clip 50 blocks blood from being supplied into the hemorrhoids 12, and thus the hemorrhoids 12 are separated off.

In addition, in a state where the banana clip 50 is positioned to encircle the hemorrhoids 12, particularly, the clip applier 30, included in a surgical tool set 20 described below, presses a pressing surface 33c (FIG. 2) against tissue in the vicinity of the hemorrhoids 12. Thus, the banana clip 50 is positioned in the vicinity of the roots of the hemorrhoids 12.

The banana clip 50 includes a clip main-body and a holding guide. The clip main-body has a first clip arm and a second clip arm that are connected to each other by a flexible bending portion in a manner that maintains a predetermined bend angle with respect to each other. The first clip arm and the second clip arm are closed with an outside force in a state where the hemorrhoids 12 to be removed are interposed therebetween, and thus are tied tightly around the hemorrhoids 12. When the clip main-body is bent inward, the holding guide prevents the first clip arm and the second clip from being slid off the hemorrhoids 12 therebetween.

In addition, the surgical tool set includes the banana clip 50 for removing the hemorrhoids 12, and the clip applier 30. The banana clip 50 for removing the hemorrhoids 12 includes the clip main-body and the holding guide. The clip main-body has the first and second clip arms that are connected to each other by the flexible bending portion in a manner that maintains a predetermined bend angle with respect to each other. The first and second clip arms are closed with the outside force in the state where the hemorrhoids 12 to be removed are interposed therebetween, and thus are tied tightly around the hemorrhoids 12. When the clip main-body is bent inward, the holding guide guides relative motions of the first and second clip arms with respect to each other and thus prevents misalignment between the first and second clip arms. The clip applier 30 picks up the banana clip 50, positions the first and second clip arms in the vicinity of the hemorrhoids 12 to be removed, closes the first and second clip arms, and ties the first and second clip arms tightly around the hemorrhoids 12.

Figure 2:
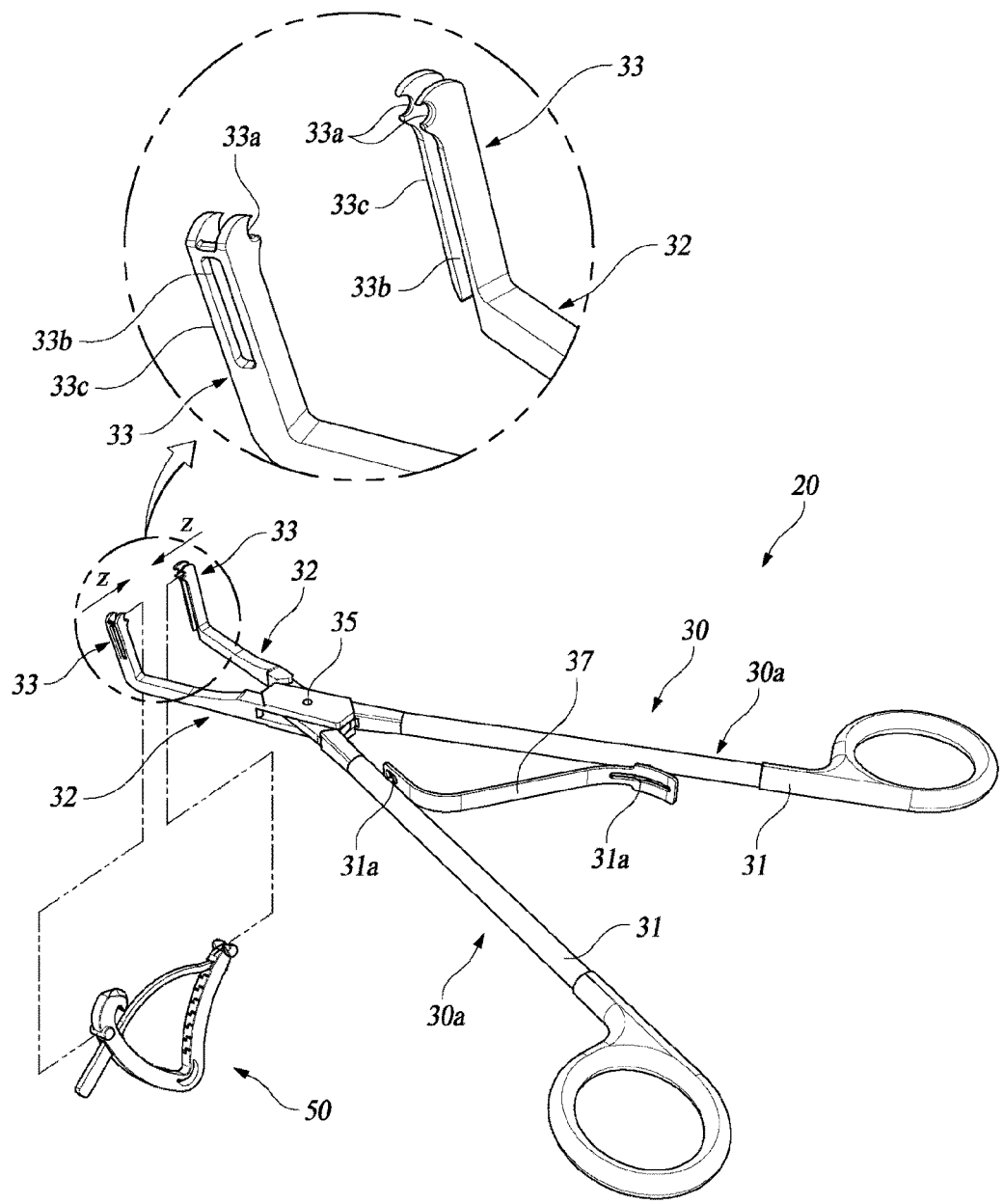
FIG. 2 is a perspective exploded view illustrating a surgical tool set according to an embodiment of the present disclosure.
Figure 3:
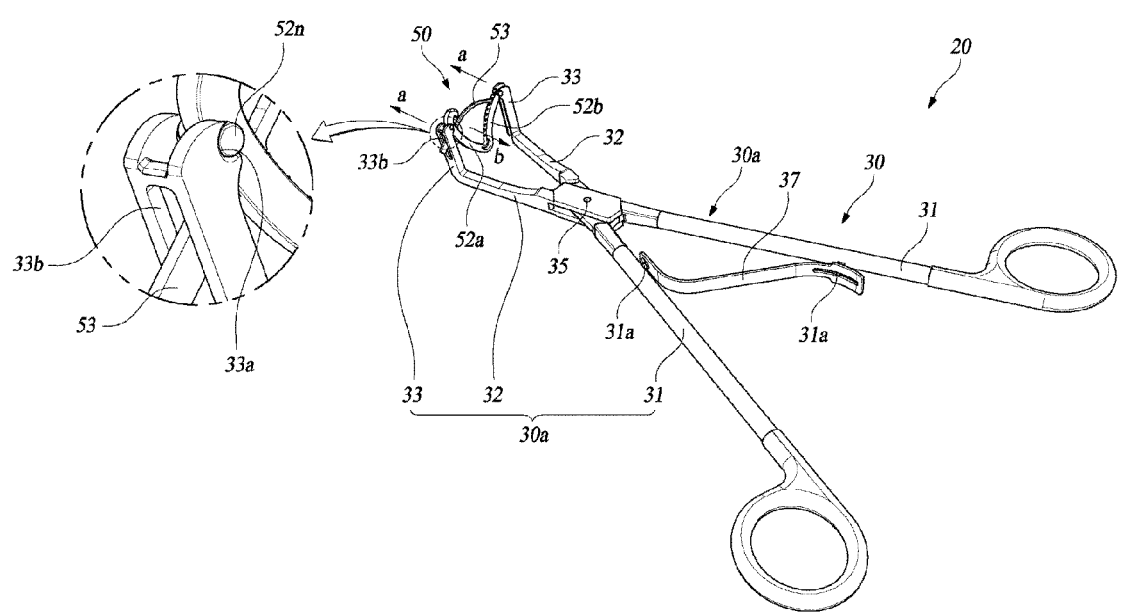
FIG. 3 is a perspective view illustrating that a clip applier illustrated in FIG. 2 picks up a banana clip.

FIG. 2 is a perspective exploded view illustrating the surgical tool set 20 according to an embodiment of the present disclosure. FIG. 3 is a perspective view illustrating that the clip applier 30 illustrated in FIG. 2 picks up the banana clip 50.

As illustrated, the surgical tool set 20 according to the present embodiment includes the banana clip 50 and the clip applier 30. The banana clip 50 is tied tightly around the hemorrhoids 12 to be removed. The clip applier 30 is a tool that picks up the banana clip 50 and ties the banana clip 50 tightly around the hemorrhoids 12.

First, a detailed configuration of the banana clip 50 is described with reference to FIG. 4.

Figure 4:
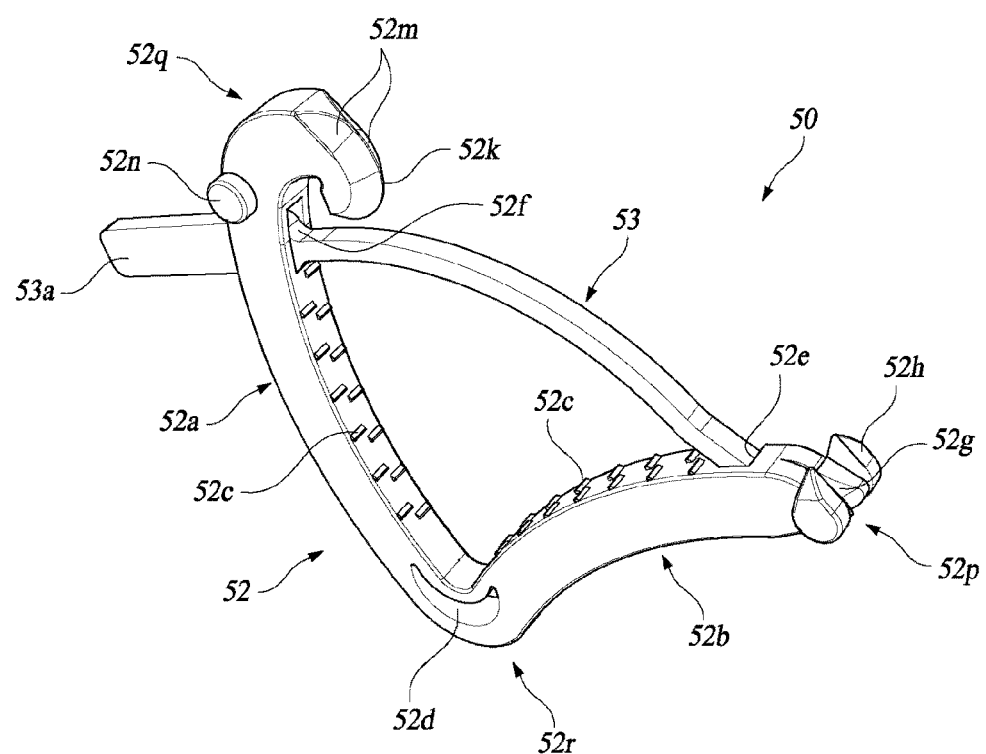
FIG. 4 is a perspective view separately illustrating a banana clip for removing hemorrhoids according to an embodiment of the present disclosure.

As illustrated in FIG. 4, the banana clip 50, made of flexible synthetic resin, includes a clip main-body 52 and a holding guide 53. The clip main-body 52 is bent inward at the predetermined bend angle.

The clip main-body 52 has a bending portion 52r, a first clip arm 52a, and a second clip arm 52b. The first clip arm 52a and a second clip arm 52b, integrally combined with the bending portion 52r, are opened at the predetermined bend angle. The first clip arm 52a and the second clip arm 52b each are curved to a constant curvature. The first clip arm 52a and the second clip arm 52b, when the outside force is not applied thereto, are kept curved, as illustrated in FIG. 4. The first clip arm 52a and the second clip arm 52b, when tied tightly around the hemorrhoids 12, are brought into contact with each other and thus has the form of a banana, as illustrated in FIG. 5d.

Slippage prevention protrusions 52c are formed on each of the respective opposing surfaces of the first and second clip arms 52a and 52b. The slipping prevention protrusions 52c serve as slipping prevention portions that prevent each of the first and second clip arms 52a and 52b from being slid along the hemorrhoids 12. While the ligation is in progress, or in a state where the ligation is finished, the slipping prevention protrusions 52c serve to prevent the first and second clip arms 52a and 52b from being slid along the hemorrhoids 12. Another reason for providing in this manner the slippage prevention protrusions 52c that protrude as the sliding prevention portions is to more effectively press the slipping prevention protrusions 52c against blood vessels in the hemorrhoids 12 and thus completely block blood from flowing through the hemorrhoids 12.

Moreover, a hook portion 52q is provided on an end portion of the first clip arm 52a, and a ligation-keeping portion 52p is provided on an end portion of the second clip arm 52b. The hook portion 52q, like a hook, is bent back. As illustrated in FIG. 5d. The hook portion 52q is engaged with the ligation-keeping portion 52p, and thus the first and second clip arms 52a and 52b are kept tied tightly around the hemorrhoids 12.

In addition, a guide groove 52g with the top side open is formed in an upper surface of the ligation-keeping portion 52p. The guide groove 52g is brought into contact with the hook portion 52q immediately before the first and second clip arms 52a and 52b are brought into contact with each other, and guides a motion of the hook portion 52q, thereby preventing misalignment between the first and second clip arms 52a and 52b. That is, the hook portion 52q is guided in such a manner as not to move sideways.

A directional motion in which the first and second clip arms 52a and 52b are closed and a directional motion in which the first and second clip arms 52a and 52b are opened are hereinafter collectively referred to a rotational motion.

A center edge portion 52k is formed on the hook portion 52q. The center edge portion 52k, when inserted into the guide groove 52g, is supported on the guide groove 52g. The center edge portion 52k is a sharp arc-shaped portion formed on a center portion, in the width direction, of the first clip arm 52a. The center edge portion 52k is brought into linear contact with the deepest bottom of the guide groove 52g and thus is supported on the guide groove 52g. That is, immediately before the hook portion 52q is engaged with the ligation-keeping portion 52p, the center edge portion 52k is supported in a state of being inserted into the guide groove 52g.

An inclination portions 52m is formed on both sides of the center edge portion 52k. The inclination portions 52m are portions that, when the hook portion 52q is introduced into an upper portion of the ligation-keeping portion 52p, are guided by second pressing protrusions 52h described below. When the center edge portion 52k is smoothly guided by the hook portion 52q, the inclination portions 52m are not brought into contact with the second pressing protrusions 52h, respectively.

Moreover, a jaw portion 52s is formed on a front-end portion of the first clip arm 52a. The jaw portion 52s, as illustrated in FIG. 5d, passes over the ligation-keeping portion 52p and is engaged with an upper end portion of the first clip arm (52b), thereby being kept held in place.

first pressing protrusions 52n are formed on both sides, respectively in the width direction, of the end portion of the first clip arm 52a. The first pressing protrusions 52n are force application portions that transfer an outside force acting thereon to the first clip arm 52a. The first pressing protrusions 52n are inserted into support grooves 33a, respectively, in the clip applier 30. That is, in a state where the first pressing protrusions 52n are inserted into the support grooves 33a, a clip pressing portion 33 exerts a pushing force, in an z-direction indicated by an arrow, on the first pressing protrusions 52n.

In addition, a guide hole 52f is formed in the end portion of the first clip arm 52a, and a guide holding groove 52e is formed in an end portion of the second clip arm 52b.

The guide hole 52f is a rectangular hole that is pierced, in the rotational direction of the first clip arm 52a, through the first clip arm 52a. A holding guide 53 described below passes through the guide hole 52f.

Moreover, the guide holding groove 52e is a groove accommodating and supporting a front-end portion of the holding guide 53. The front-end portion of the holding guide 53 is inserted into the guide holding groove 52e and is supported thereon. It is possible that the holding guide 53 is easily separated from the guide holding groove 52e. For example, for the separation of the holding guide 53, a user can pull the holding guide 53 with his/her one hand while holding the second clip arm 52b with his/her other hand. After the clip main-body 52 is tied tightly around the hemorrhoids 12, the holding guide 53, as illustrated in FIG. 5d, is separated from the guide holding groove 52e.

The second pressing protrusions 52h are provided on the end portion of the second clip arm 52b. Like the first pressing protrusions 52n, the second pressing protrusions 52h serve as force application portions that transfer an outside force acting thereon to the second clip arm 52b. Likewise, a pushing force is also exerted, in a z-direction indicated by an arrow, on the second pressing protrusions 52h inserted into the support grooves 33a in the clip applier 30.

The bending portion 52r connecting the first clip arm 52a and the second clip arm 52b to each other is integrally combined with the first and second clip arms 52a and 52b. The bending portion 52r provides a supporting force in such a manner that the first and second clip arms 52a and 52b are closed or opened. Particularly, a transformation guidance hole 52d is formed in the bending portion 52r.

When the first and second clip arms 52a and 52b are closed, the transformation guidance hole 52d serves to facilitate transformation of the bend portion 52r and to prevent concentration of stress on the bending portion 52r. In this manner, the formation of the transformation guidance hole 52d makes it possible to close the first and second clip arms 52a and 52b more smoothly. Furthermore, since low stress acts on the bending portion 52r, there is no concern that the bending portion 52r will be split or broken in a state where the ligation is finished, The holding guide 53 is a curved bar-shaped member that is made of the same material as the clip main-body 52. A front-end portion of the holding guide 53 passes through the guide hole 52f and then is inserted into the guide holding groove 52e, thereby being held in place. As described above, it is possible that the holding guide 53 is separable from the guide holding groove 52e with the user's finger. Reference character 53a denotes a handle that is used when the holding guide 53 is separated from the second clip arm 52b.

When the first clip arm 52a and the second clip arm 52b are closed, the holding guide 53 serves to block the first clip arm 52a and the second clip arm 52b from being slid off the hemorrhoids 12 interposed therebetween.

As illustrated in FIGS. 2 and 3, the clip applier 30 has approximately the shape of scissors and has the clip pressing portion 33 on a front-end portion thereof. The banana clip 50 is inserted between the clip pressing portions 33 and thus is bent inward. The clip applier 30 serves to pick up the banana clip 50, position the first and second clip arms 52a and 52b in the vicinity of the hemorrhoids 12 and tie the first and second clip arms 52a and 52b tightly around the hemorrhoids 12.

The clip applier 30 is configured with a pair of applier halves 30a that are movably fastened together by a connection pin 35 in such a manner as to cross each other. The applier halves 30a are fastened together by the connection pin 35 and move in a way resembling the action of scissors.

Each of the applier halves 30a includes a handle 31, an extension portion 32, and the clip pressing portion 33. The connection pin 35 is positioned between the handle 31 and the extension portion 32.

The handle 31 is held with the user's hand. For example, the user opens or closes the applier halves 30a with his/her fingers and thumb inserted into holes in the handles 31. In addition, the extension portion 32 is connected to the handle 31 with the connection pin 35 interposed therebetween. The extension portion 32 is integrally combined with the handle 31.

The clip pressing portion 33 is integrally combined with an end portion of the extension portion 32. Particularly, the clip pressing portion 33 is bent to a bend angle of approximately 90 degrees with respect to the extension portion 32.

The reason for bending the clip pressing portion 33 in this manner is to press the pressing surface 33c of the clip pressing portion 33 against a region in the vicinity of the hemorrhoids 12 in the direction a indicated by an arrow in FIG. 3. In other words, in a state where the hemorrhoids 12 are positioned within a space formed by the first and second clip arms 52a and 52b and the holding guide 53, the clip applier 30 is pressed in the direction a indicated by the arrow. Thus, the hemorrhoids 12 passing through such a space are positioned by the greatest possible distance in the direction b indicated by an arrow away from the first and second clip arms 52a and 52b and the holding guide 53. In this manner, the banana clip 50 is positioned up to the vicinity of roots of the hemorrhoids 12 and, in some cases, is positioned beyond the vicinity of the roots thereof.

The support grooves 33a and accommodation slits 33b are formed in each of the clip pressing portions 33. The first pressing protrusions 52n and the second pressing protrusions 52h are accommodated into the support grooves 33a on one of the clip pressing portions 30 and the support grooves 33a on the other of the clip pressing portions 30, respectively, that are open in a manner that faces each other. The pushing force is applied to the first pressing protrusions 52n and the second pressing protrusions 52h. The first and second clip arms 52a and 52b are accommodated into the accommodation slits 33b, respectively.

Reference character 37 denotes a leaf spring. Both end portions of the leaf spring 37 are supported on spring holding grooves 31a, respectively. The spring holding grooves 31a are formed in the applier halves 30a, respectively. The leaf spring 37 keeps the handles 31 open. With operation of the leaf spring 37, the clip pressing portions 33 are kept open in a state where an outside force is applied thereto.

FIGS. 5A to 5D are views each illustrating operation of the surgical tool set 20 according to the embodiment of the present disclosure.

First, the banana clip 50 to be used is inserted between the clip pressing portions 33. At this point, of course, the first pressing protrusions 52n and the second pressing protrusions 52h of the banana clip 50 need to be inserted into the support grooves 33a on one of the clip pressing portions 30 and the support grooves 33a on the other of the clip pressing portions 30, respectively.

When the preparation step described above is finished, as illustrated in FIG. 5a, the hemorrhoids 12 are caused to pass through a space between the first and second clip arms 52a and 52b in a state where the first and second clip arms 52a and 52b are opened. Then, the clip applier 30 is pressed in the direction a indicated by the arrow in FIG. 3, thereby positioning the roots of the hemorrhoids 12 between the first and second clip arms 52a and 52b.

Subsequently, the handles 31 are brought together to close the first and second clip arms 52a and 52b in the direction z in FIG. 2. Thus, the hook portion 52q is engaged with the ligation-keeping portion 52p. At this point, the first and second clip arms 52a and 52b are pressed and thus is tied tightly around hemorrhoids 12 in a state where the hemorrhoids 12 interposed between the first and second clip arms 52a and 52b are held in place among the holding guide 53 and the first and second clip arms 52a and 52b.

Figure 5A:
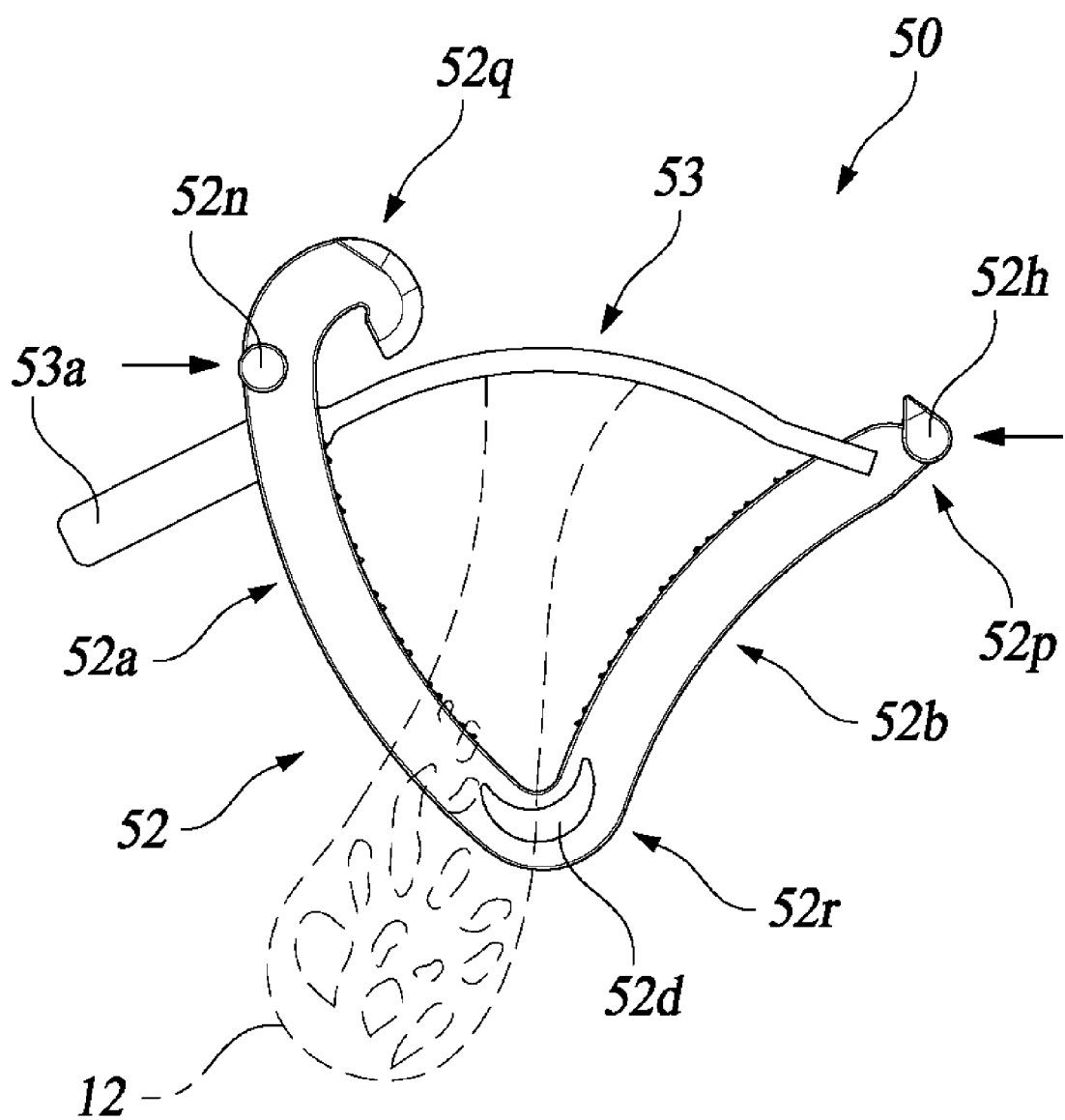
FIGS. 5A to 5D are views sequentially illustrating a method of using a surgical tool set according to an embodiment of the present disclosure.
Figure 5B:
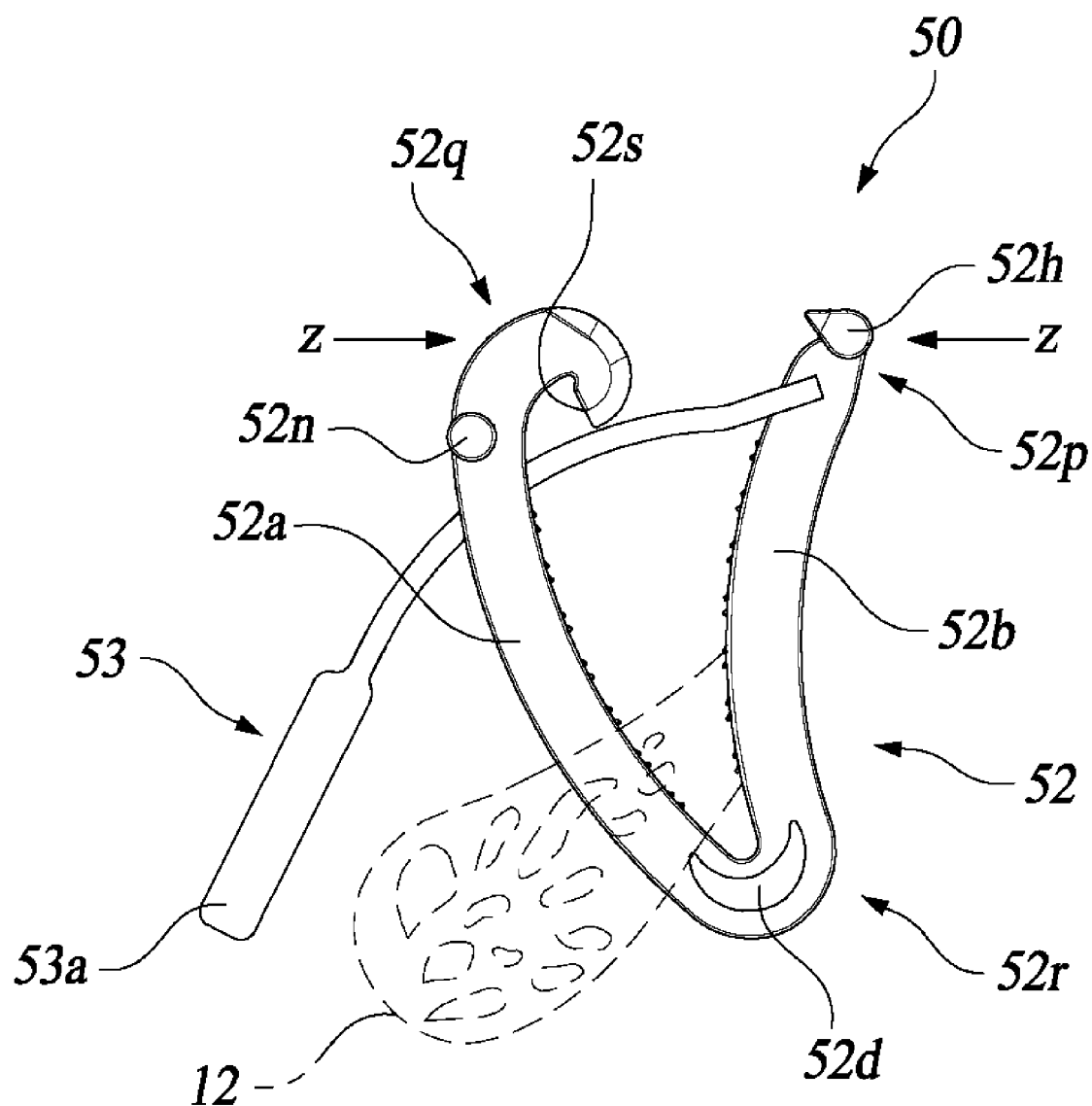
Figure 5C:
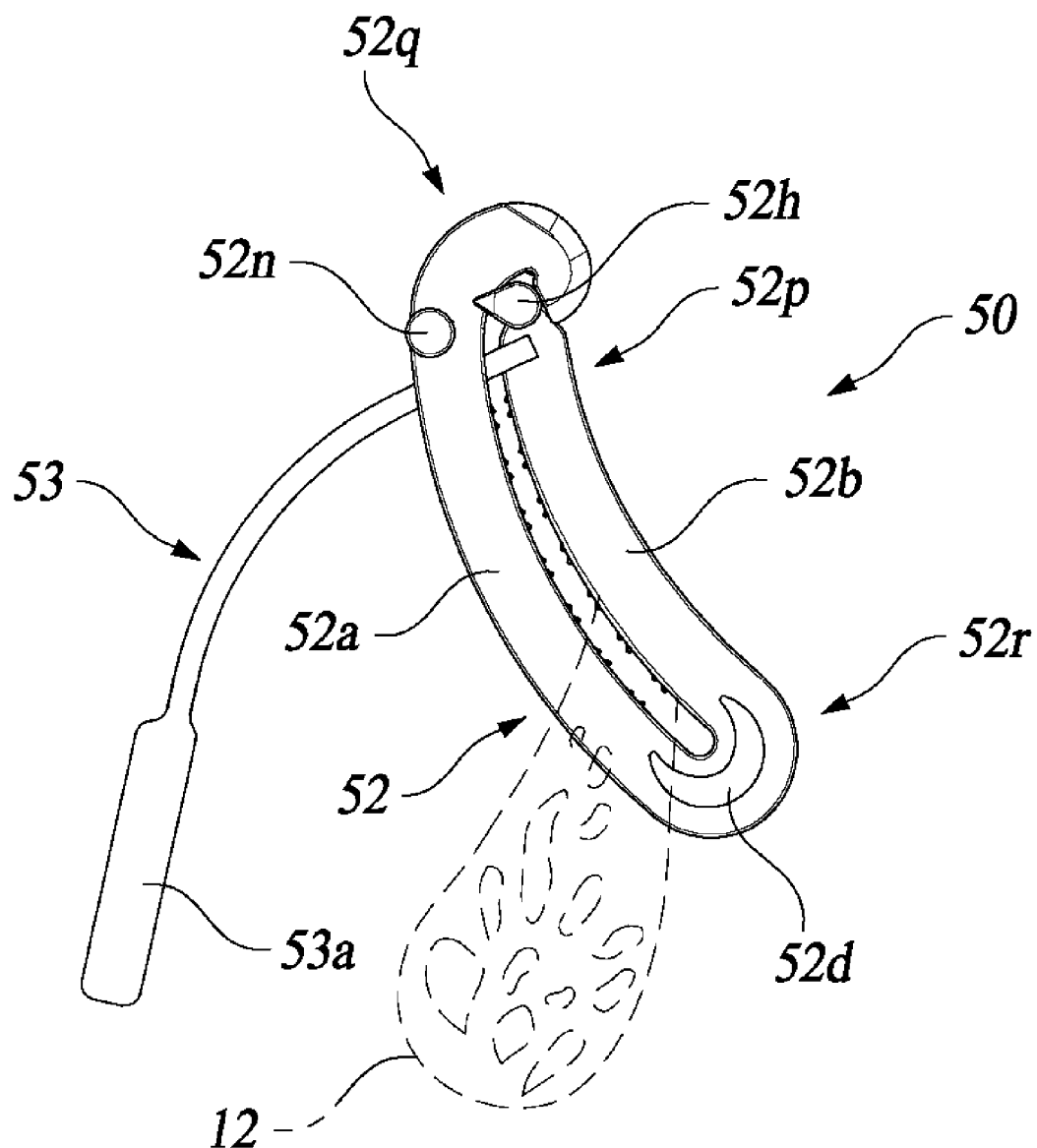
Figure 5D:
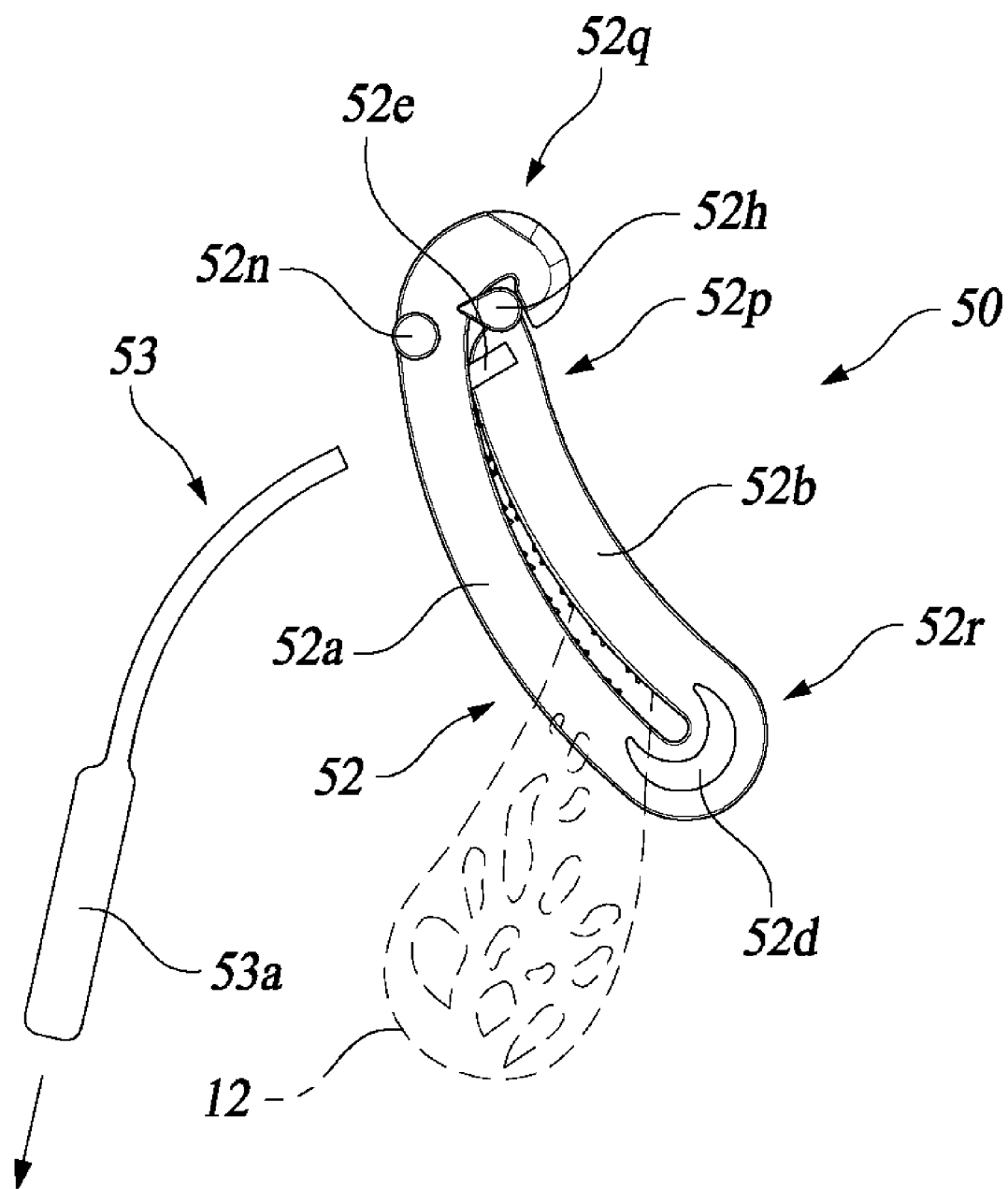

As illustrated in FIG. 5c, when finishing the ligation, the user removes the holding guide 53 from the clip main-body 52 that is tied tightly around the hemorrhoids 12 to finish the operation on the hemorrhoids 12. The holding guide 53 is for providing alignment between the first and second clip arms 52a and 52b that are suture materials. After the ligation is finished, the holding guide 50 is no longer necessary, and therefore is removed.

The specific embodiment of the present disclosure is described in detail above. However, the present disclosure is not limited to the specific embodiment. It would be apparent to a person of ordinary skill in the art that various modifications to the present disclosure are possible within the scope of the technical idea of the present disclosure.

The invention claimed is:

1. A banana clip for removing hemorrhoids, the banana clip comprising:
  a clip main-body comprising a first clip arm and a second clip arm, connected to each other by a flexible bending portion in a manner that maintains a predetermined bend angle with respect with each other, which are configured to close with an outside force in a state where the hemorrhoids to be removed are interposed therebetween and thus are configured to be tied tightly around the hemorrhoids; and
  a holding guide, connecting the first clip arm and the second clip arm to each other which is configured to hold the hemorrhoids in place between the first clip arm and the second clip arm when the clip main-body is bent inward,
  wherein a guide hole is formed in the first clip arm in a manner that is pierced in a rotational direction of the first clip arm, and
  a front-end portion of the holding guide is configured to pass through the guide hole and then be removably combined with the second clip arm, and, when the first and second clip arms are closed or opened, the holding guide is supported on an internal surface of the guide hole.

2. The banana clip of claim 1, wherein a hook portion and a ligation-keeping portion, which are configured to be engaged with each other and to maintain a state where the first clip arm and the second clip arm are brought into contact with each other, said hook portion and ligation-keeping portion are formed on end portions, respectively, of the first clip arm and the second clip arm.

3. The banana clip of claim 2, wherein the hook portion is formed on the end portion of the first clip arm, and the ligation-keeping portion is formed on the end portion of the second clip arm, and
  a guide groove which is configured such that, immediately before the first and second clip arms are brought into contact with each other, the guide groove can be brought into contact with the hook portion and thus guide a motion of the hook portion and prevent misalignment between the first and second clip arms, said guide groove is formed in the ligation-keeping portion, and a center edge portion, which is configured to be supported on the guide groove while inserted into the guide groove, is provided on the hook portion.

4. The banana clip of claim 1, wherein a force application portion is configured to transfer an outside force acting thereon to each of the first and second clip arms, is provided on an end portion of each of the first and second clip arms.

5. The banana clip of claim 1, wherein slippage prevention portions are configured to prevent each of the first and second clip arms from sliding along the hemorrhoids, and are formed on each of the respective opposing surfaces of the first and second clip arms.

6. The banana clip of claim 1, wherein the first and second clip arms are curved to a constant curvature, and
  a transformation guidance hole is formed in the flexible bending portion, the transformation guidance hole is configured to facilitate transformation of the bending portion and thus prevent concentration of stress on the bending portion when the first and second clip arms are closed.

7. A surgical tool set comprising:
  the banana clip of claim 1; and
  a clip applier, configured to: a) pick up the banana clip, b) position the first and second clip arms in the vicinity of the hemorrhoids to be removed, and c) close the first and second clip arms, and thus tie the first and second clip arms tightly around the hemorrhoids,
  wherein the clip applier is configured with a pair of applier halves movably fastened together by a connection pin in such a manner as to cross each other, and
  wherein each of the applier halves comprises:
    a handle;
    an extension portion connected to the handle with the connection pin interposed therebetween; and
    a clip pressing portion, integrally combined with an end portion of the extension portion, said clip pressing portion is configured to press the first and second clip arms in a direction of closing the first and second clip arms, wherein the clip pressing portions of both applier halves each have a bend at a predetermined bend angle with respect to the extension portions, respectively, and the predetermined bend angle is in a plane which is orthogonal to the plane in which the applier halves are configured to open and close.

8. The surgical tool set of claim 7, wherein accommodation slits are formed on inside surfaces, respectively, of the clip pressing portions, the first and second clip arms are configured to be accommodated into and supported on the inside surfaces, respectively, when the banana clip is bent inward.

9. The surgical tool set of claim 8, wherein first pressing protrusions and second pressing protrusions are provided on an end portion of the first clip arm and an end portion of the second clip arm, respectively, the first pressing protrusions and the second pressing portions, both of which are configured to transfer outside forces acting thereon to the first and second clip arms, respectively, and support grooves are further formed in each of the clip pressing portions, the first pressing protrusions and the second pressing protrusions are configured to be accommodated into and supported on the support grooves in one of the clip pressing portions and the support grooves in the other of the clip pressing portions, respectively.

10. The surgical tool set of claim 8, wherein a hook portion and a ligation-keeping portion are configured to be engaged with each other and maintain a state where the first and second clip arms are in contact with each other, said hook portion and the ligation-keeping portion are formed on end portions, respectively, of the first and second clip arms.

11. The surgical tool set of claim 10, wherein the hook portion is formed on the end portion of the first clip arm, and the ligation-keeping portion is formed on the end portion of the second clip arm, and a guide groove, which is configured such that, immediately before the first and second clip arms are brought into contact with each other, the guide groove can be brought into contact with the hook portion and thus guide a motion of the hook portion and prevent misalignment between the first and second clip arms, said guide groove is formed in the ligation-keeping portion, and a center edge portion, which is configured to be supported on the guide groove while inserted into the guide groove, is provided on the hook portion.

12. The surgical tool set of claim 8, wherein slippage prevention portions are configured to prevent each of the first and second clip arms from sliding along the hemorrhoids, and are formed on each of respective opposing surfaces of the first and second clip arms.

13. The surgical tool set of claim 8, wherein the first and second clip arms are curved to a constant curvature, and a transformation guidance hole is formed in the bending portion, the transformation guidance hole is configured to facilitate transformation of the bending portion and thus prevent concentration of stress on the bending portion when the first and second clip arms are closed.

14. The surgical tool set of claim 8, wherein the clip pressing portions of both applier halves have a 90 degree bend angle with respect to the extension portions, respectively.

* * * * *